US00PP34772P3

(12) United States Plant Patent
Slavchev

(10) Patent No.: US PP34,772 P3
(45) Date of Patent: Nov. 29, 2022

(54) RASPBERRY PLANT NAMED 'YANA'

(50) Latin Name: ***Rubus idaeus* L.**
Varietal Denomination: YANA

(71) Applicant: EU PLANTS LTD, Finchampstead (GB)

(72) Inventor: Slavey Slavchev, Finchampstead (GB)

(73) Assignee: EU PLANTS LTD OF MANOR FARM, Finchampstead (GB)

( * ) Notice: Subject to any disclaimer, the term of this patent is extended or adjusted under 35 U.S.C. 154(b) by 0 days.

(21) Appl. No.: 17/164,322

(22) Filed: Feb. 1, 2021

(65) Prior Publication Data

US 2021/0243928 P1 Aug. 5, 2021

(30) Foreign Application Priority Data

Jan. 30, 2020 (QZ) ..... PBR 2020/0331

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204, 203
CPC ..... A01H 5/0887
See application file for complete search history.

(56) References Cited

U.S. PATENT DOCUMENTS

PP32,722 P2 * 1/2021 Vitten ..... A01H 1/106 Plt./204
PP32,948 P2 * 4/2021 Rodriguez Mesa ..... Plt./204

OTHER PUBLICATIONS https://www.facebook.com/ChambersFruit/videos/irena-and-paloma-from-chambers-espa%C3%B1a-are-excited-about-the-new-yana-raspberry-c/405106160547553/; Jan. 14, 2021; 1 page.*
Google search page; May 8, 2021; 1 page.*

* cited by examiner

*Primary Examiner* — Kent L Bell
(74) *Attorney, Agent, or Firm* — Alston & Bird LLP

(57) ABSTRACT

Described is a new and distinct cultivar of red raspberry, *Rubus ideaus* L., and referred herein by the variety denomination of the red raspberry plant named 'YANA'.

7 Drawing Sheets

Latin name of the genus and species: *Rubus idaeus* L.

Variety denomination: The Raspberry Plant Named 'YANA'.

CROSS-REFERENCE TO RELATED APPLICATIONS

This application claims priority to and the benefit of European Union (EU) Community Plant Variety Application No. 2020/0331, filed Jan. 30, 2020; the entire contents of which as are hereby incorporated by reference herein.

BACKGROUND

The present invention is directed toward a new and distinct cultivar of red raspberry, *Rubus idaeus* L., and referred herein by the variety denomination the Raspberry Plant Named 'YANA'. The Raspberry Plant Named 'YANA' was produced from seeds and unknown cross-breeding. More particularly, seeds were collected from fruit brought from British supermarkets in 2013 and were grown in the Summer of 2014 in Oxfordshire, England. The seeds pollinated in the Autumn in open fields. In 2015, 40,000 seeds produced as described were sown and produced 6,000 seedlings. These seedlings were crossed in the Spring of 2016 and one variety selected was collected and termed the Raspberry Plant Named 'YANA'. The resulting raspberry plants have been asexually reproduced repeatedly by in vitro propagation and by soft cuttings of shoots from the roots, since that time. The variety of the present invention has been found to retain its distinctive characteristics through successive asexual propagation in Oxfordshire, England.

BRIEF SUMMARY

Generally described, the present invention exhibits multiple distinguishing characteristics, as will be detailed herein-below.

The following are some of the distinguishing characteristics of this new cultivar variety of raspberry plant, namely the Raspberry Plant Named 'YANA', when grown under normal horticultural practices in Oxfordshire, England:

- Primocane raspberry plant.
- Shape and size of leaves.
- Exceptional fruit presentation.
- Great fruit shape.
- Great looks and tastes, as compared to most Primocane varieties.
- Good shelf-life and looks, as compared to known varieties.
- Colour of the dormant cane.

BRIEF DESCRIPTION OF THE PHOTOGRAPHS

The patent or application file contains at least one drawing or photograph executed in color. Copies, as required, have been submitted with this patent or application.

The new variety of raspberry plant, namely the Raspberry Plant Named 'YANA', is illustrated by the accompanying photographs which show the fruit of the plant as well as the Primocanes; the colours shown are true as according to conventional photographic procedures. The photographs in FIGS. 1 to 4 are of one-year old plants.

DETAILED BOTANICAL DESCRIPTION

The present invention now will be described more fully hereinafter with reference to the accompanying drawings. The description provided herein is intended to ensure that this disclosure will satisfy applicable legal requirements. Unless where otherwise noted, the data that define these characteristics are based on observations taken from 'YANA' plants that were two years old and grown at a farm located at Garford, Abingdon, Oxfordshire, OX13 5PD, United Kingdom. The raspberry plant named 'YANA' generally grows well in USDA Zones 8 and 9.

The following description of a raspberry plant named 'YANA' sets out distinctive characteristics of the raspberry plant named 'YANA'. The description is based on UPOV terminology. Depending on environmental, seasonal, climatical or other conditions, the characteristics may vary in accordance with expected horticultural practice.

TABLE 1

Similar Varieties and Differences from these Varieties

| Denomination of similar variety | Characteristic in which the similar variety is different | State of expression of similar variety | State of expression of 'YANA' |
|---|---|---|---|
| 'Kwanza' (unpatented) | Drupelets | Double drupelets | Round drupelets |
| 'Polka' (unpatented) | Colour and taste | Less taste, darker colour | More taste, lighter colour |
| 'Diamond Jubilee' (U.S. Pat. No. 25,455) | Drupelets | Double drupelets | Round drupelets |
| 'Glen Amble' (unpatented) | Shelf life | Short shelf life | Long shelf life |

III. Shelf-Life Testing

Raspberry fruit from plant named 'YANA' and a variety of commercial varieties—'Malling Bella' (unpatented), 'Malling Charm' (unpatented), 'Diamond Jubilee', and 'Maravilla' (unpatented)—to provide a practical commercial comparison were kept at room temperature 20-25 degrees, for 8 days. 'Malling Charm' raspberries degraded most rapidly. The 'Diamond Jubilee', 'Maravilla', 'YANA', and 'Malling Bella' raspberries lasted the same time before becoming too soft and mould starting to appear. The test was repeated with fresh fruit keeping the raspberry fruit in a fridge at 4 degrees. The same results were recorded after 10 days as with the ambient temperature tests. These tests show the good shelf life of the raspberry plant named 'YANA'.

These results demonstrate that the raspberry plant named 'YANA' has comparable shelf-life characteristics compared with current commercial raspberry varieties.

IV. Taste

The raspberry plant named 'YANA' produces sweet tasting raspberry fruit. It has relatively high sugar content, however it has a distinct strong raspberry taste. It is also very juicy which may be due to its size. Being bigger it holds more juice. It is very tasty in the sense of it having a classic raspberry taste and because it is very juicy it creates a very good balance.

V. Appearance of the Fruit

Figure 1:
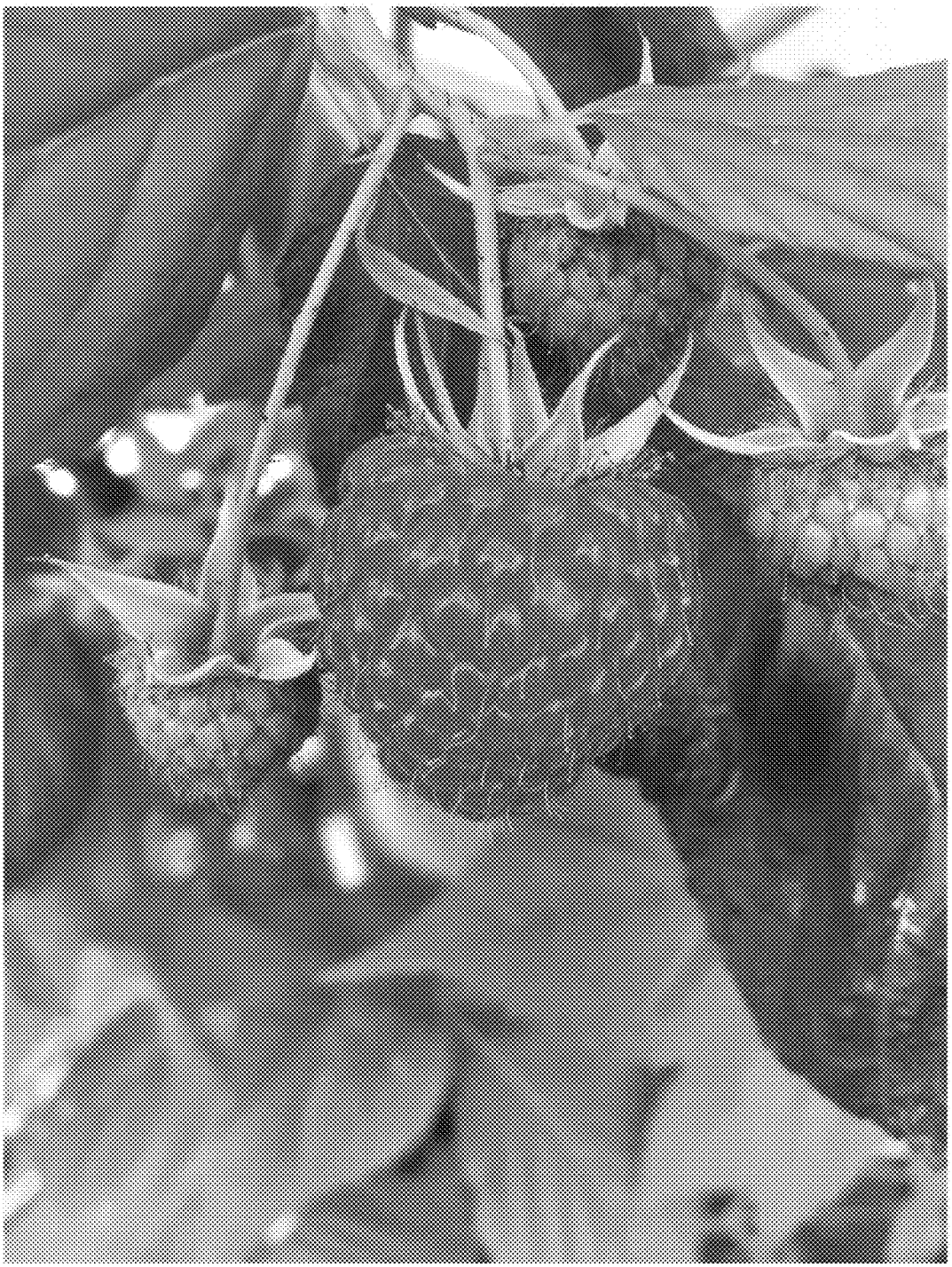
FIG. 1 shows the shape and dimensions of the fruit of the Raspberry Plant Named 'YANA'.
Figure 2:
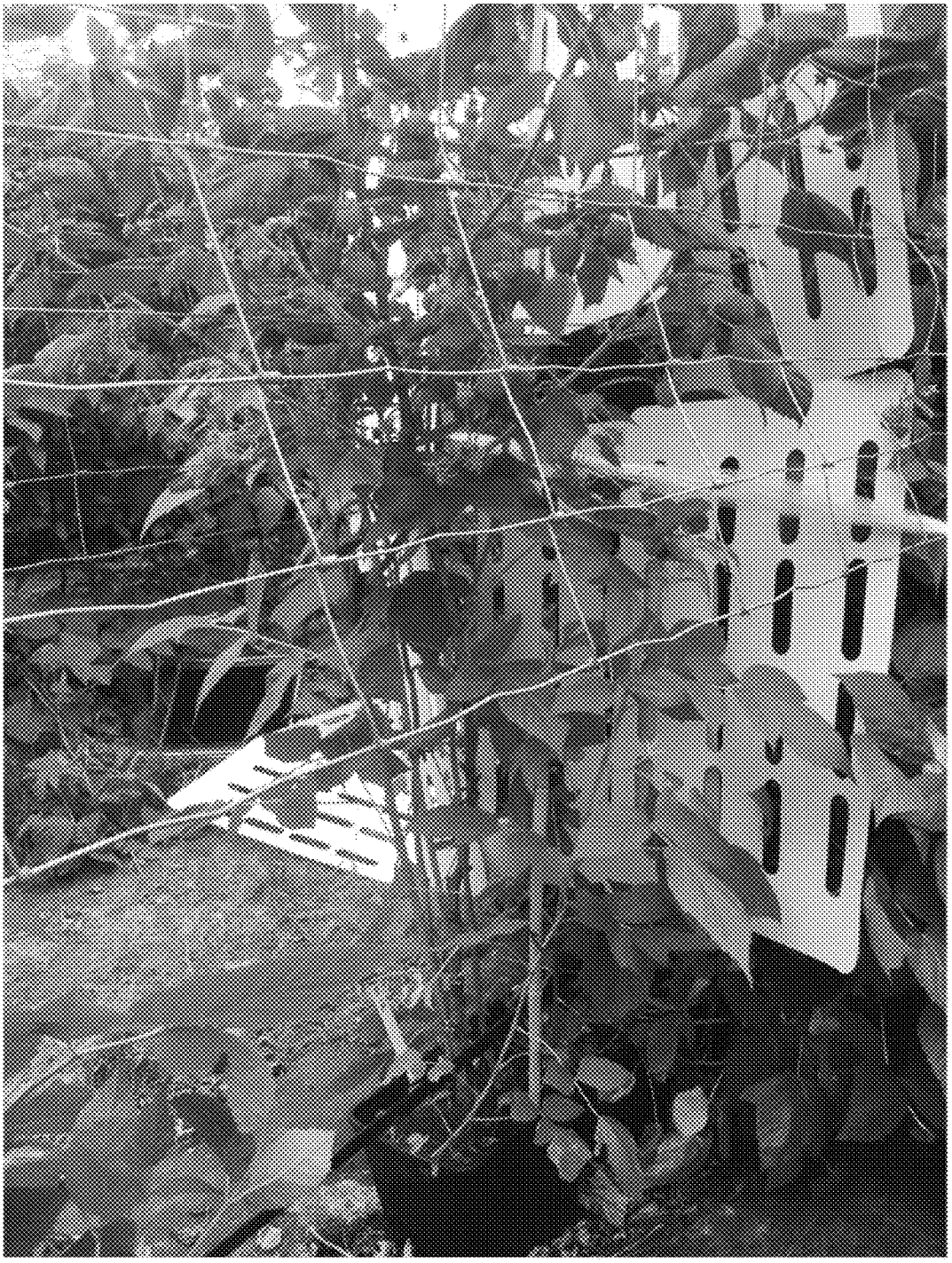
FIG. 2 shows the shape and conformation of the Raspberry Plant Named 'YANA' including leaf shape.
Figure 3:
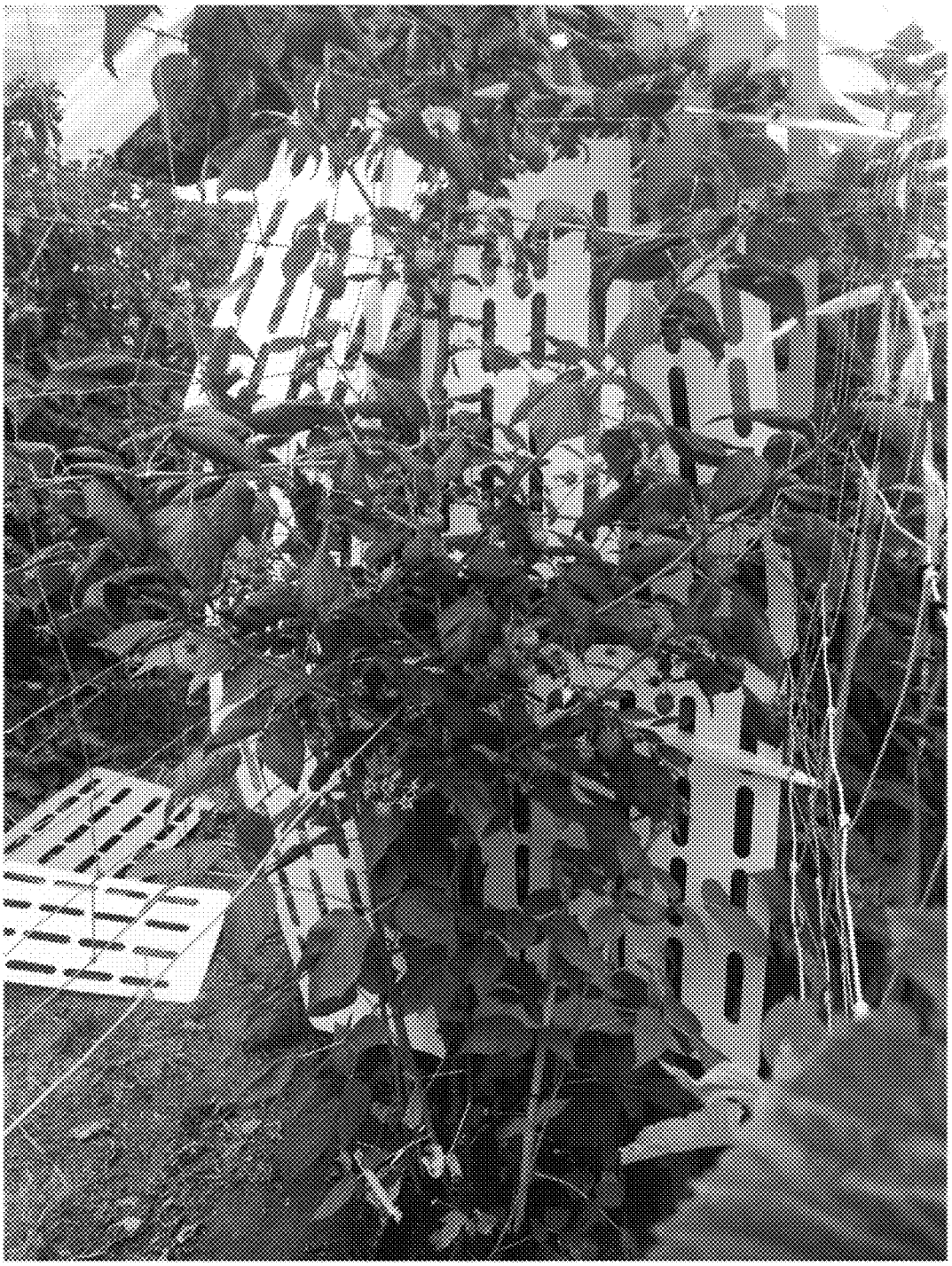
FIG. 3 shows the shape and conformation of the Raspberry Plant Named 'YANA' including leaf shape.
Figure 4:
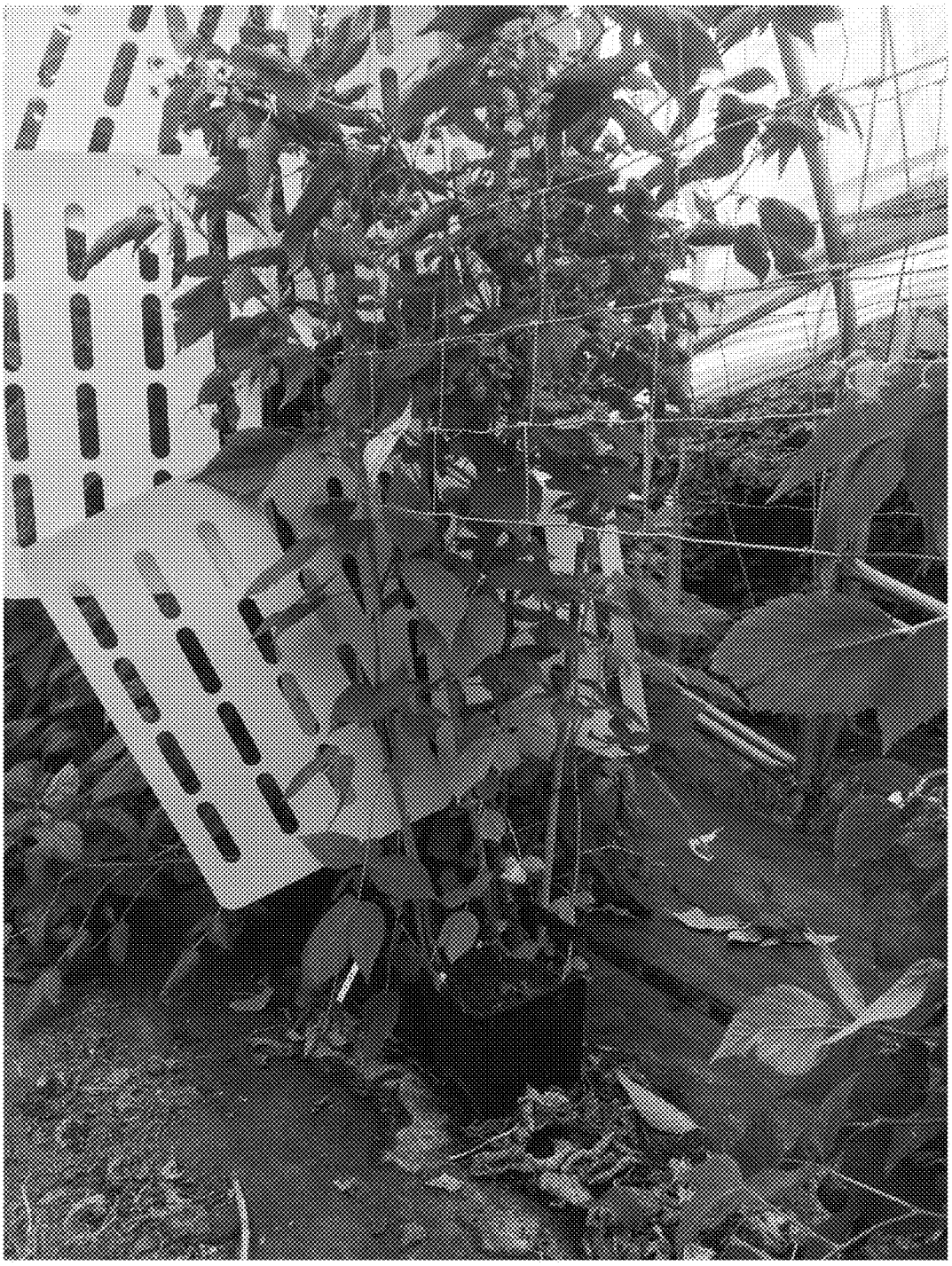
FIG. 4 shows the shape and conformation of the Raspberry Plant Named 'YANA'.
Figure 6:
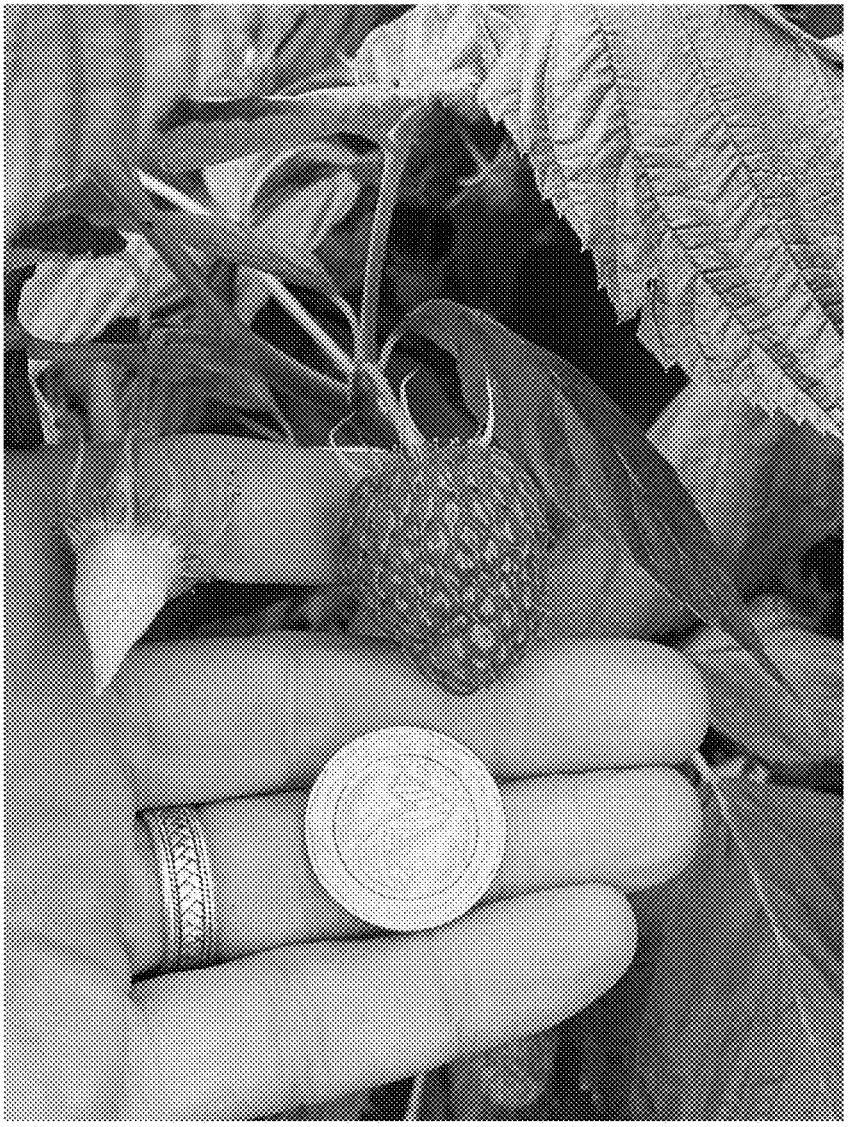
FIG. 6 shows the typical size of the Raspberry Plant Named 'YANA' raspberry fruit compared to a coin of about 27 mm.

It has a quite unique and distinctive characteristic. The raspberries as shown particularly in FIGS. 1 and 6 are particularly glossy in appearance. The single drupelet being single probably contributes a lot the glossiness of the berry and the raspberry plant named 'YANA' the glossiest berry known to the applicant.

VI. Appearance of the 'YANA' Raspberry Plants

Figure 5:
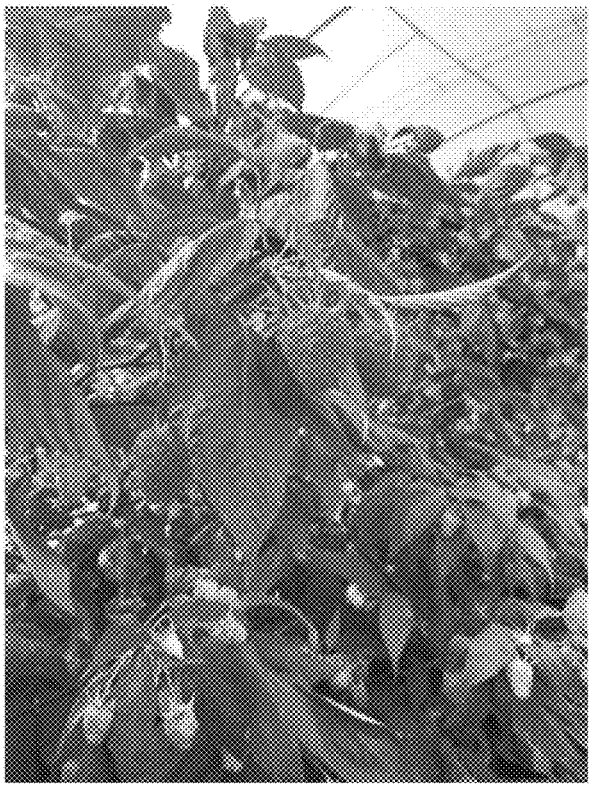
FIG. 5 shows the distinctive leaf shape of the Raspberry Plant Named 'YANA' (upper picture) and size compared to a typical commercial variety (lower picture).
Figure 5:
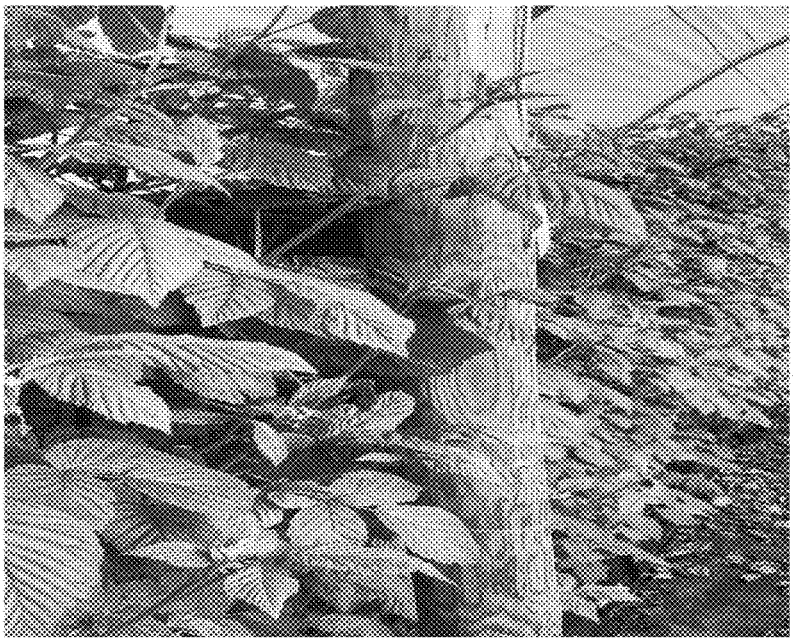
Figure 7:
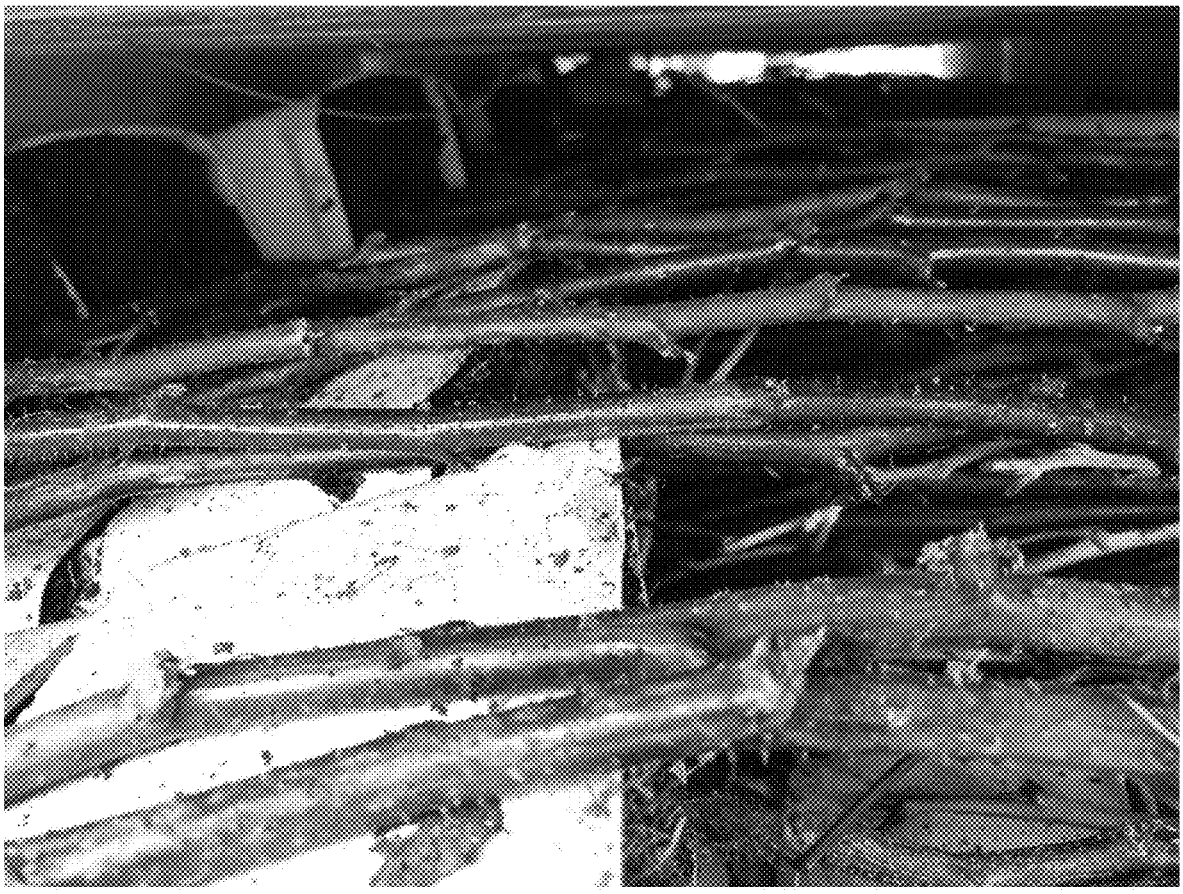
FIG. 7 shows the nature of the cane colour and spine size and numbers of the Raspberry Plant Named 'YANA'.

A combination of all its separate features makes the raspberry plant named 'YANA' distinctive. The leaf shape and curve shown in the photographs are quite distinctive. The leaves are smaller than typical conventional varieties as shown in FIG. 5. It has relatively large spines as shown in FIG. 7. More, and bigger than 'Maravilla', 'DJ' (unpatented), and 'Tulameen' (unpatented). The spines have a slight purplish tint to them (while the cane is green, as detailed elsewhere herein), with reference to RHS Color Code N79B. There are 4-5 spines per square centimeter of area (i.e., approximately 15 spines per square inch); the spines are rose-like, but smaller in scale than conventional rose spines. Stated otherwise, the spines are small and short, but solid. A typical and observed dimension of the spines is $2/16^{th}$ of an inch long.

The slightly purplish brown (see RHS color code 167A) of the dormant raspberry plant named 'YANA' cane is also a rare feature amongst raspberry plants. The root establishment of the raspberry plant named 'YANA' is very good and quite quick, so it creates a dense root system that is also distinguishable from most other varieties. Its reproductive capabilities are also unseen with any other variety. It produces triple the tips from one root block in comparison to Maravilla for example.

Color(s) referenced herein and considered distinctive have been described and positively identified by a recognized color dictionary or color chart, namely The Horticultural Colour Chart of The Royal Horticultural Society, London, England (R.H.S. Colour Chart). Specifically, the medium red color referenced elsewhere herein is RHS color code 43B; this is also distinctively shiny. The dormant slight purplish brown color referenced elsewhere herein is RHS color code 167A. The purplish tint of the spines referenced elsewhere herein is RHS color code N79B.

The raspberry plant named 'YANA' grows well when pot grown in 100% coir substrate. More specifically, the raspberry plant named 'YANA' is to be planted in May, with the plants grown in unheated poly tunnels. Harvesting is in May of the same year; or more generally, harvesting within a month of planting. A typical and observed amount of fruit harvested per season at the location referenced elsewhere herein is about 1.6 kg per cane.

In terms of disease and insect resistance, the raspberry plant named 'YANA' has been found to be resistant to *Phytophthora* and spider mite.

In terms of height and width, the raspberry plant named 'YANA' is typically 1.5 meters in cane height and 1.3 centimeters in cane thickness at about 1.2 meters of the height. The primocanes of the raspberry plant named 'YANA' are typically 150 centimeters long, with 1.3 centimeter-wide cane and 5-6 centimeter apart evenly spaced internodes. For fruiting, the raspberry plant named 'YANA' is usually planted at 4 canes per linear meter.

Lateral shoots of the raspberry plant named 'YANA' are typically 80 centimeters long, 0.6 centimeters wide, with RHS color code 142A. The growth habit of the raspberry plant named 'YANA' is bushy.

Leaves of the raspberry plant named 'YANA' typically comprise three leaflets. The leaves are roughly 13 centimeters long by 7 centimeters wide, while fruiting. Leaflets of the raspberry plant named 'YANA' are typically colored on their top (i.e., sun-facing) side by RHS color code 144B. The opposing bottom side of the leaflets are typically colored by RHS color code 142C. The leaflets of the raspberry plant named 'YANA' are typically 19 centimeters long by 13 centimeters wide. The typical and observed leaflet shape is aristate (i.e, having a long bristle at its apex, a pointed, beard-like process, a slender, sharp, spiny tip), the margins of the leaflets are serrulated (i.e., having or denoting a jagged edge; saw-like), and the texture of both major surfaces of the leaflets is smooth.

Flowers of the raspberry plant named 'YANA' are typical and observed as having white petals (both surfaces, through most stages of growth), with a flower depth of about 5 millimeters (0.2 inches) and a flower width of about 10 millimeters (0.4 inches). In relation to the petals of the raspberry plant named 'YANA', the plant flowers typically have 5-6 petals, each having dimensions of about 8 millimeters (0.3 inches) long and about 4 millimeters (0.16 inches) wide. The petals are typical and observed as having an elongated raindrop shape; they also have a single margin. The apex of the petals is rounded, and the texture of either surface thereof is smooth.

Sepals of the raspberry plant named 'YANA' are typical and observed as numbering five (5). The sepals are generally triangular with an elongate thread-like tail at the top. The sepals are also typically observed as being about 10 millimeters (0.4 inches) long. The sepals have no margins, and the texture of either surface is smooth. The color of the upper surface of the sepals is 142C, and the color of the lower surface of the sepals is 142B.

The raspberry plant named 'YANA' further has peduncles with a typical length, in a less than mature plant, of about 5 centimeters (1.96 inches). The typical length of the peduncles in a mature plant is about 6 centimeters (2.36 inches). The texture of the peduncles is smooth, while the color thereof is primarily 142B, with some redness (46A) in certain areas.

For reproductive organ purposes, the raspberry plant named 'YANA' includes, as described previously herein, at least the following combination of features: each flower having 5-6 white (RHS Color Code NN155D) petals, a ring of anthers, 100-125 pistils, and 8-160 ovaries.

Petioles of the raspberry plant named 'YANA' have a typical length of 13 centimeters and a diameter of 3 millimeters, with RHS color code of 145A. The stipules of the raspberry plant named 'YANA' have color of RHS color code 145A. The stipules are small and thin, being about 1-2 centimeters long, but with a thickness of about 1 millimeter.

Fruit of the raspberry plant named 'YANA' is typically 3.5 to 4.0 centimeters long, with a width of 2.5 centimeters. Individual fruit weight is between 10 and 12 grams. Fruit shape in lateral view is broad conical and color is medium red (RHS 43B). Berry adherence to plug is medium. Fruit length to width ratio is medium. The fruit ripens on the previous year's canes beginning in May and bears fruit in the Summer. The fruit of the raspberry plant named 'YANA' is used for domestic and commercial consumption, having very good shipping qualities.

That which is claimed:

1. A new and distinct cultivar of raspberry plant, 'YANA', substantially as illustrated and described, characterized by its fruit shape, leaf appearance, and taste.

* * * * *